United States Patent
Kim et al.

(10) Patent No.: US 11,867,216 B2
(45) Date of Patent: Jan. 9, 2024

(54) COMPLIANT SELF-ANCHORING SCREW WITH AUXETIC PROPERTIES

(71) Applicants: Hando Kim, Los Angeles, CA (US); Jonathan B Hopkins, Los Angeles, CA (US)

(72) Inventors: Hando Kim, Los Angeles, CA (US); Jonathan B Hopkins, Los Angeles, CA (US)

(73) Assignee: Hando Kim, Los Angeles, CA (US)

(*) Notice: Subject to any disclaimer, the term of this patent is extended or adjusted under 35 U.S.C. 154(b) by 195 days.

(21) Appl. No.: 17/332,603

(22) Filed: May 27, 2021

(65) Prior Publication Data
US 2022/0074442 A1 Mar. 10, 2022

Related U.S. Application Data

(60) Provisional application No. 63/034,737, filed on Jun. 4, 2020.

(51) Int. Cl.
*F16B 31/04* (2006.01)
*F16B 25/00* (2006.01)
(Continued)

(52) U.S. Cl.
CPC .......... *F16B 31/04* (2013.01); *F16B 25/0094* (2013.01); *A61B 17/863* (2013.01); *A61B 17/8685* (2013.01); *F16B 25/103* (2013.01)

(58) Field of Classification Search
CPC .... F16B 31/04; F16B 25/0094; F16B 25/103; F16B 35/041; F16B 13/063; F16B 5/0241;
(Continued)

(56) References Cited

U.S. PATENT DOCUMENTS 1,168,770 A * 1/1916 Wagner ................. F16B 13/124
411/80.1
1,373,045 A * 3/1921 Bernhard ................ F16B 39/08
411/522
(Continued)

FOREIGN PATENT DOCUMENTS

CN 107981926 B 3/2021

OTHER PUBLICATIONS

Yao Y, Wang L, Li J, Tian S, Zhang M, Fan Y, "A novel auxetic structure based bone screw design: Tensile mechanical characterization and pullout fixation strength evaluation," Materials & Design (Mar. 2020) vol. 188:108424 https://doi.org/10.1016/j.matdes.2019.108424.

*Primary Examiner* — Victor D Batson
*Assistant Examiner* — Dil K. Magar (57) ABSTRACT

The present invention provides compliant screws compatible with standard threaded holes that are self-anchoring via auxetic properties. Once a screw has been twisted in place using a mating screw driver, the screw won't be able to be removed unless it is broken, its surrounding material is torn out with the screw, or unless the screw driver itself is again used to twist the screw in the opposite direction. Thus, although reusable, the screw will never come out of its hole in the presence of vibrations or other cyclic or random loading scenarios. The screws are thereby suitable for critical joint applications where screws must never come loose. Non-limiting examples include satellite fasteners, high-speed vehicle bolts, pedicle screws, and other screws used to secure medical implants within a human body.

18 Claims, 5 Drawing Sheets

(51) Int. Cl.
  *F16B 25/10* (2006.01)
  *A61B 17/86* (2006.01)
(58) Field of Classification Search
  CPC ........ F16B 35/02; F16B 21/086; F16B 7/025; F16B 7/0413; A61B 17/863; A61B 17/8685
  USPC ............... 411/383, 271, 325, 333, 508–510, 411/417–419
  See application file for complete search history.

(56) References Cited

U.S. PATENT DOCUMENTS

| | | | | |
|---|---|---|---|---|
| 2,511,512 | A * | 6/1950 | Poupitch | F16B 13/122 411/508 |
| 2,560,211 | A * | 7/1951 | Burdick | F16B 35/00 411/383 |
| 2,564,638 | A * | 8/1951 | Churchill | F16B 21/086 411/446 |
| 3,077,809 | A * | 2/1963 | Harding | E21D 11/006 411/33 |
| 3,921,496 | A * | 11/1975 | Helderman | F16B 13/126 411/455 |
| 4,395,174 | A * | 7/1983 | Freeman | F16B 15/06 411/510 |
| 4,396,329 | A * | 8/1983 | Wollar | F16B 21/084 411/452 |
| 4,427,328 | A * | 1/1984 | Kojima | F16B 21/084 24/625 |
| 4,475,856 | A | 10/1984 | Toomingas | |
| 4,568,215 | A * | 2/1986 | Nelson | B29C 66/474 24/297 |
| 4,571,136 | A * | 2/1986 | Peek | F16B 37/0842 411/510 |
| 4,728,238 | A * | 3/1988 | Chisholm | F16B 19/004 411/510 |
| 4,900,210 | A * | 2/1990 | Buchanan | F16B 33/006 411/510 |
| 4,936,530 | A * | 6/1990 | Wollar | F16B 13/02 248/68.1 |
| 5,197,840 | A * | 3/1993 | Peek | F16B 37/0842 411/433 |
| 5,312,214 | A * | 5/1994 | Morton | F16B 37/12 411/324 |
| 5,360,188 | A * | 11/1994 | Condon | F16L 5/02 174/152 G |
| 5,417,692 | A * | 5/1995 | Goble | A61B 17/7291 606/328 |
| 5,695,307 | A * | 12/1997 | Takahashi | F16B 5/0642 411/482 |
| 5,765,787 | A * | 6/1998 | de Beers | F16L 3/237 248/74.2 |
| 5,868,537 | A * | 2/1999 | Latal | F16B 21/084 411/510 |
| 5,971,334 | A * | 10/1999 | Crawshaw | F16M 13/022 411/383 |
| 6,345,946 | B1 * | 2/2002 | Mainini | F16B 21/086 411/339 |
| 6,517,543 | B1 * | 2/2003 | Berrevoets | A61B 17/68 411/419 |
| 6,613,053 | B1 * | 9/2003 | Collins | A61B 17/7059 606/293 |
| 6,719,513 | B1 * | 4/2004 | Moutousis | F16B 21/084 411/510 |
| 6,804,864 | B2 * | 10/2004 | Kirchen | F16B 5/0642 24/297 |
| 7,004,702 | B2 * | 2/2006 | Van Der Heijden | F16B 37/0842 411/438 |
| 7,329,076 | B2 * | 2/2008 | Hartney | F16B 39/028 411/60.1 |
| 7,503,528 | B2 * | 3/2009 | Adams | F16L 3/137 24/297 |
| 7,896,601 | B2 * | 3/2011 | Kalyanadurga | F16B 21/084 411/510 |
| 8,533,919 | B2 * | 9/2013 | Schliessner | F16B 5/0685 24/297 |
| 9,211,153 | B2 | 12/2015 | Fisher et al. | |
| 9,241,808 | B2 | 1/2016 | Sabatino | |
| 9,677,589 | B2 * | 6/2017 | Koelling | F16B 21/082 |
| 9,681,905 | B2 | 6/2017 | Reimels | |
| 10,064,669 | B2 | 9/2018 | Garvey | |
| 10,111,690 | B2 * | 10/2018 | Anderson | A61B 17/7233 |
| 2003/0082026 | A1 * | 5/2003 | Brletich | F16B 21/084 411/311 |
| 2003/0206784 | A1 * | 11/2003 | Huang | F16B 13/002 411/29 |
| 2006/0183079 | A1 * | 8/2006 | Galvan | A61B 17/863 433/174 |
| 2006/0239795 | A1 * | 10/2006 | Jaconelli | F16B 35/044 411/383 |
| 2007/0043372 | A1 * | 2/2007 | Willmann | A61B 17/863 606/264 |
| 2007/0134073 | A1 * | 6/2007 | Shereyk | F16B 21/084 411/510 |
| 2007/0233123 | A1 * | 10/2007 | Ahmad | A61B 17/864 606/307 |
| 2008/0183220 | A1 * | 7/2008 | Glazer | A61B 17/686 606/301 |
| 2010/0190138 | A1 * | 7/2010 | Giorno | A61B 17/863 433/174 |
| 2010/0217329 | A1 * | 8/2010 | Brown | A61B 17/742 606/301 |
| 2011/0313473 | A1 * | 12/2011 | Prandi | A61B 17/8635 606/315 |
| 2012/0259372 | A1 * | 10/2012 | Glazer | A61B 17/686 606/301 |
| 2014/0194937 | A1 * | 7/2014 | Asnis | A61B 17/8645 606/316 |
| 2015/0078901 | A1 * | 3/2015 | Milne | F01D 5/066 403/299 |
| 2015/0219136 | A1 * | 8/2015 | Koelling | F16B 21/084 411/510 |
| 2015/0230844 | A1 * | 8/2015 | Ellis | A61B 17/8635 606/316 |
| 2018/0028288 | A1 | 2/2018 | Haus | |
| 2019/0125498 | A1 | 5/2019 | Bernhard | |
| 2019/0331258 | A1 * | 10/2019 | Geiger | F16L 3/2332 |

* cited by examiner

COMPLIANT SELF-ANCHORING SCREW WITH AUXETIC PROPERTIES

BACKGROUND OF THE INVENTION

Existing monolithic screws are static in design with a rudimentary screw head, screw shank, and screw threading. After being driven into a material, the screws are unable to dynamically respond to changes in the material, including but not limited to vibrations, cyclic loads, and random loads. Over time, these screws will loosen and inevitably fail.

Thus, there is a need in the art for improved screw designs capable of responding to dynamic loads. The present invention meets this need.

SUMMARY OF THE INVENTION

In one aspect, the present invention relates to a compliant, self-anchoring screw with auxetic properties, comprising: a proximal screw head; a screw shank extending distally from the screw head; a plurality of blade flexures extending from the screw shank in a proximal direction at an angle relative to a longitudinal axis of the screw shank, the plurality of blade flexures being linearly aligned to form at least two row of blade flexures along the screw shank; a panel attached to each row of blade flexures; and a screw thread positioned on an exterior surface of each panel, the screw thread being continuous across all panels; wherein the screw comprises a resting state and a loaded state.

In one embodiment, the screw shank has a proximal diameter and a distal diameter, the distal diameter defining a central shaft. In one embodiment, the plurality of blade flexures extend from the central shaft beyond the proximal diameter of the screw shank. In one embodiment, the proximal diameter is greater than, equal to, or less than the distal diameter.

In one embodiment, each blade flexure has a cross-sectional shape that is rectangular or trapezoidal. In one embodiment, each blade flexure has a profile that is rectangular or trapezoidal. In one embodiment, the plurality of blade flexures comprises varied thicknesses, such that each row of blade flexures is ordered with a thickest thickness at a distal end and a thinnest thickness at a proximal end.

In one embodiment, the screw shank further comprises one or more rings extending from the central shaft, each ring being positioned immediately distal to a blade flexure. In one embodiment, a ring is positioned at a distal end of the central shaft and at a midpoint of a length of the central shaft.

In one embodiment, the screw thread is longer at a proximal end and gradually decreases towards a distal end. In one embodiment, each panel is positioned equidistantly around the screw shank. In one embodiment, all panels are connected to each other at a distal end to form a distal tip. In one embodiment, the distal tip is selected from the group consisting of: a flat end, a slight taper, a pointed tip, a self-tapping tip, and a self-drilling tip.

In one embodiment, the resting state of the screw positions the distal tip flush against a distal end of the screw shank. In one embodiment, the resting state of the screw maintains a gap between the distal tip and a distal end of the screw shank. In one embodiment, the loaded state of the screw tensions each panel in a distal direction relative to the screw head and the screw shank, such that each blade flexures bend outwards and expands each panel outwards away from the screw shank. In one embodiment, the loaded state of the screw compresses each panel in a proximal direction relative to the screw head and the screw shank, such that each blade flexure bends inwards and compacts each panel inwards towards the screw shank.

In one embodiment, the screw shank comprises an indent encircling the screw shank, the indent forming a distal wall, and wherein each panel comprises a panel shelf that extends into the indent, such that the distal wall blocks the panel shelf when each panel is overtensioned in a distal direction. In one embodiment, the distal wall is angled in a distal direction, and wherein the panel shelf of each panel has an angled surface facing the distal wall, such that the distal wall pushes the panel shelf outwards away from the screw shank when each panel is overtensioned in a distal direction.

In one embodiment, the screw shaft, each of the panels, and combinations thereof comprise a textured or perforated surface that increases its surface area to volume ratio.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

DETAILED DESCRIPTION

The present invention provides compliant screws compatible with standard threaded holes that are self-anchoring via auxetic properties. Once a screw has been twisted in place using a mating screw driver, the screw won't be able to be removed unless it is broken, its surrounding material is torn out with the screw, or unless the screw driver itself is again used to twist the screw in the opposite direction. Thus, although reusable, the screw will never come out of its hole in the presence of vibrations or other cyclic or random loading scenarios. The screws are thereby suitable for critical joint applications where screws must never come loose. Non-limiting examples include satellite fasteners, high-speed vehicle bolts, pedicle screws, and other screws used to secure medical implants within a human body.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein.

The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Compliant Self-Anchoring Screw

Figure 1:
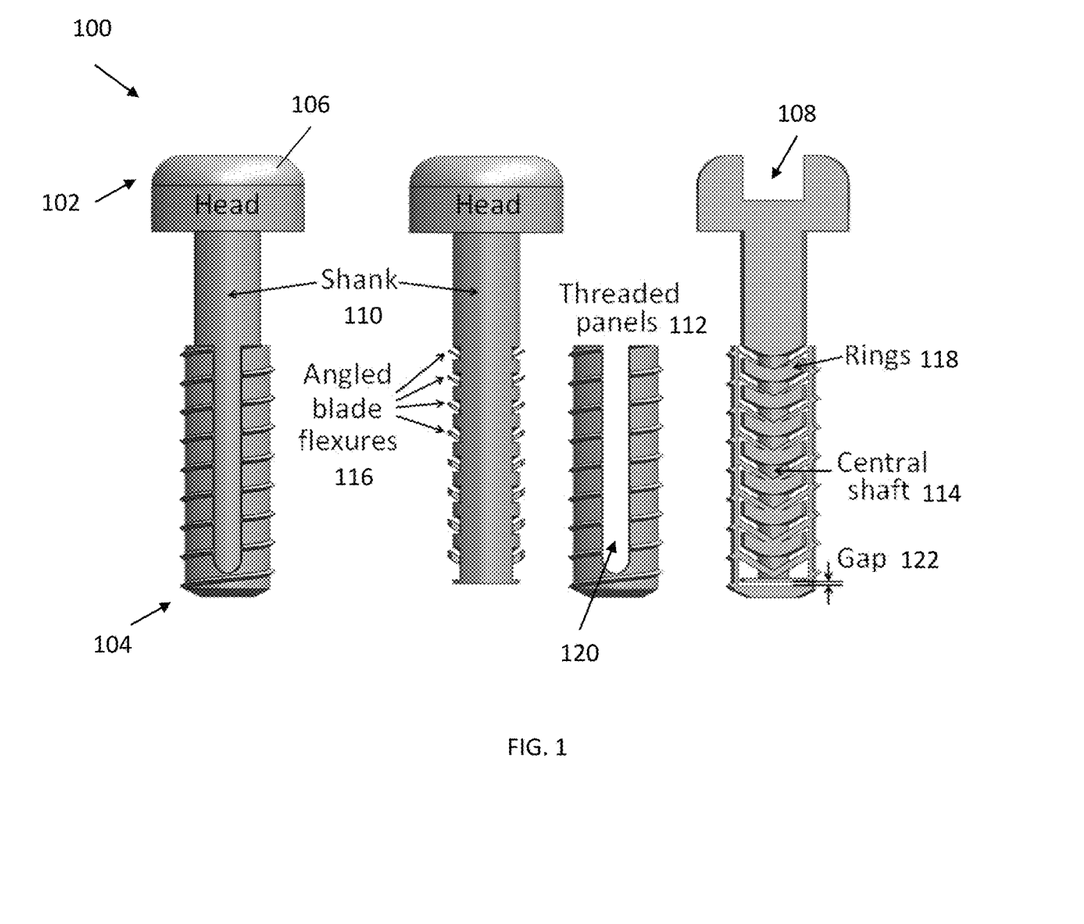
FIG. 1 depicts side and cross-sectional views of an exemplary screw.

Referring now to FIG. 1, an exemplary screw 100 is depicted. Screw 100 comprises a proximal end 102, a distal end 104, a proximally positioned head 106 and a distally positioned shank 110. Head 106 can be any desired head as would be understood by those having skill in the art, including but not limited to countersunk heads, non-countersunk heads, flat heads, round heads, polygonal heads (such as square, pentagonal, hexagonal, etc.), and the like. In some embodiments head 106 can comprise a smooth distal surface or a textured distal surface. Head 106 can comprise screw drive 108, which can be any desired drive as would be understood by those having skill in the art, including but not limited to slot drives, cross drives, Phillips drives, Torx drives, internal polygonal drives (such as triangle, square, hexagonal, etc.), and the like.

Figure 2:
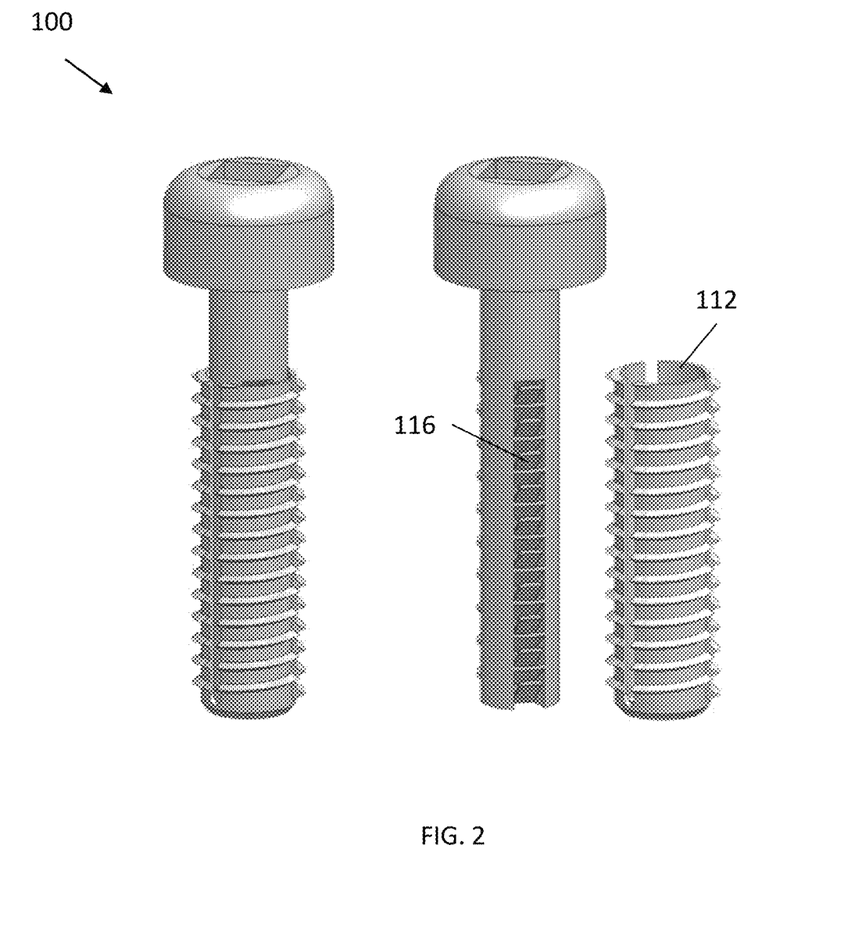
FIG. 2 depicts perspective views of an exemplary screw.

Shank 110 extends from head 106 in a proximal direction. Shank 110 comprises a length having a proximal diameter and a distal diameter, wherein the distal diameter defines central shaft 114 of shank 110 from which a plurality of angled blade flexures 116 extend in linear alignment (also visible in FIG. 2). In various embodiments, the proximal diameter of shank 110 can be greater than, equal to, or less than the distal diameter of central shaft 114.

Each blade flexure 116 extends toward proximal end 102 by an angle relative to a longitudinal axis of shank 110. The angle can be any suitable angle, such as an angle between about 90° to about 1°. In embodiments where the proximal diameter of shank 110 is greater than the distal diameter of central shaft 114, blade flexures 116 extend beyond the outer diameter of shank 110. Blade flexures 116 can have any suitable shape. For example, in the cross-sectional view in FIG. 1, blade flexures 116 are shown having a substantially rectangular cross-sectional shape, and in the perspective view in FIG. 2, blade flexures 116 are shown having a substantially rectangular profile. In various embodiments, blade flexures 116 can have tapered or trapezoidal cross-sectional shapes and profiles that increase in width or decrease in width from central shaft 114. Blade flexures 116 can also have any suitable thickness. FIG. 1 depicts an exemplary embodiment wherein blade flexures 116 have varying thicknesses such that the distal-most blade flexures 116 are the thickest and proximally successive blade flexures 116 decrease in thickness. In this manner, a stiffness of a load path in screw 100 stays substantially balanced while in tension, as will be described elsewhere herein.

In some embodiments, screw 100 further comprises one or more rings 118 extending from central shaft 114. Rings 118 can be positioned immediately distal to a blade flexure 116. While screw 100 is under load, blade flexures 116 are bent towards distal end 104 of screw 100. The positioning of a ring 118 immediately distal to a blade flexure 116 acts as a physical stop for each blade flexure 116. Ring 118 can also be angled between about 90° and 1° relative to the longitudinal axis of shank 110 to limit and stiffen the bend of blade flexures 116. Since rings 118 add to the diameter of central shaft 114, they can also increase the torsional stiffness of central shaft 114. While rings 118 are depicted in FIG. 1 as being positioned in every space between adjacent blade flexures 116, it should be understood that screw 100 can include any number of rings 118. For example, screw 100 can include rings 118 between every other space or some other regular periodicity between adjacent blade flexures 116, or include rings 118 only at a distal position and a midpoint position on a length of central shaft 114, or include no rings 118 at all.

Threaded panel 112 is an expandable tubular panel having a continuously threaded exterior and a hollow interior. In some embodiments, the exterior threading is uniform. In some embodiments, the exterior threading is longer at a proximal end of threaded panel 112 and gradually decreases as the exterior threading approaches the distal end of threaded panel 112. While threaded panel 112 is depicted with two panels in FIG. 1 and three panels in FIG. 2, it should be understood that threaded panel 112 can comprise any desired number of panels. Each of the panels can be spaced equidstantly around central shaft 114 for isotropic pressure distribution. Each of the panels is separated by a space 120 and is joined to each other at their respective distal ends to form a distal tip. While threaded panel 112 is depicted with a flat distal tip having a slight taper, it should be understood that threaded panel 112 can have any desired distal tip, including pointed tips, self-tapping tips, and self-drilling tips.

In some embodiments, threaded panel 112 is attached to screw 100 on an interior surface of each of its panels to the proximal free end of each of the blade flexures 116 (as shown in FIG. 1, right). It should be appreciated that threaded panel 112 is connected to screw 100 only through each of the blade flexures 116. Visible in FIG. 1, screw 100 is depicted at in a resting state such that a gap 122 is maintained between the distal end of central shaft 114 and the distal end of threaded panel 112 to emphasize that threaded panel 112 is not connected to screw 100 at any other point other than bladed flexures 116. Therefore it should be appreciated that while screw 100 is depicted in FIG. 1 with gap 122, the distal end of central shaft 114 and the distal end of threaded panel 112 can be flush with each other with no space in between.

In some embodiments, threaded panel 112 is fabricated with screw 100 as a single monolithic piece. In other embodiments, threaded panel 112 can be provided as a separate piece that is attachable to screw 100 (not pictured). For example, the interior surface of each of the panels of threaded panel 112 can have a series of raised edges that blade fixtures 116 slide over when central shaft 114 is inserted into threaded panel 112 and against which blade fixtures 116 are caught on when tension is applied between threaded panel 112 and head 106.

Figure 3:
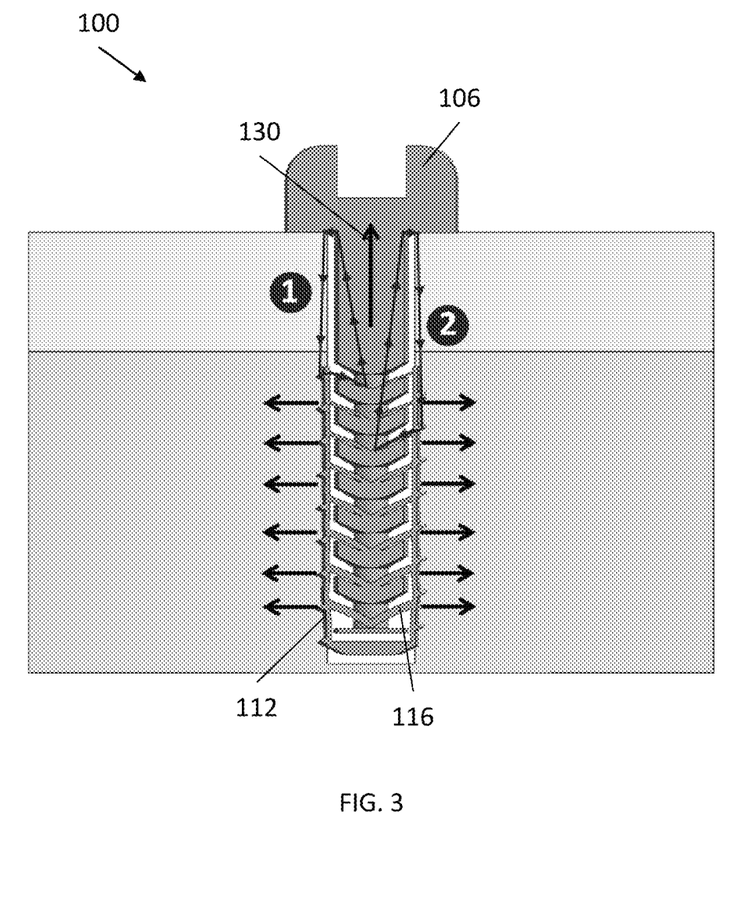
FIG. 3 depicts a cross-sectional side view of an exemplary screw self-anchoring into a substrate.

Referring now to FIG. 3, the auxetic properties of screw 100 are now described in the context of securing screw 100 into a substrate. As described above, threaded panel 112 is connected to screw 100 only by each of the blade flexures 116. Threaded panel 112 has freedom of movement in a distal direction due to its connection to blade flexures 116. For example, holding screw 100 fixed in space, moving threaded panel 112 in a distal direction expands gap 122 and simultaneously bends each connected blade flexure 116 outwards away from central shaft 114. Accordingly, each of the panels of threaded panel 112 is expanded outwards away from central shaft 114, increasing the overall diameter of threaded panel 112. In embodiments wherein screw 100 has a gap 122, threaded panel 112 can have freedom of movement in a proximal direction. For example, holding screw 100 fixed in space, moving threaded panel 112 in a proximal direction narrows gap 122 and simultaneously bends each connected blade flexure 116 inwards towards central shaft 114. Accordingly, each of the panels of threaded panel 112 is compacted inwards towards central shaft 114, reducing the overall diameter of threaded panel 112. In this manner, screw 100 can fit within a hole having a diameter slightly smaller than that of screw 100 in a resting state.

Screw 100 can be screwed into an appropriately sized hole in a manner like that of other common screws. The topology of blade flexure 116 is designed with optimal rigidity to allow head 106 to be twisted with high moment loads while still passing the desired rotational motion to threaded panel 112. In embodiments having a gap 122, threaded panel 112 is compressed as screw 100 is pushed and driven into a hole. Once the underside of head 106 reaches the surface of the substrate, further driving leads threaded panel 112 to continue to be driven in a distal direction. Meanwhile, head 106 and shank 110 cannot further progress distally due to head 106 pressing against the surface of the substrate. Therefore, the distal driving of threaded panel 112 induces an increasing tensile force 130 within the shank 110 and against head 106. When tensile force 130 is induced, blade flexures 116 are deformed in a way that causes the panels of threaded panel 112 to push outward on the walls of the hole in an auxetic fashion and thereby passively anchor screw 100 within the substrate. When screw 100 is subjected to vibrations or dynamic loading, tensile force 130 may increase. In response to additional tensile force 130, the panels of threaded panel 112 are expanded outwards even further. The securing strength of screw 100 thereby increases under higher loads.

FIG. 3 also schematically illustrates two exemplary load paths in screw 100, a shorter load path 1 and longer load path 2. Each load path extends from head 106 to a blade flexure 116. As a result, a loaded screw 100 has several load paths of varying lengths. Therefore, in some embodiments, screw 100 comprises thread and blade flexure 116 geometry that varies from the proximal end to the distal end of threaded panel 112. Since shorter load paths are typically stiffer, a varied geometry having proximal blade flexures 116 that are thinner and distal blade flexures 116 that are thicker as well as longer proximal threads and shorter distal threads balances each load path to be substantially equal such that threaded panel 112 is uniformly expanded outward such that the threading is equally engaged to the hole. This approach most efficiently uses the mass that constitutes screw 100 while distributing the stress concentrations uniformly throughout the geometry of screw 100 so that failure loads can be maximized.

Figure 4:
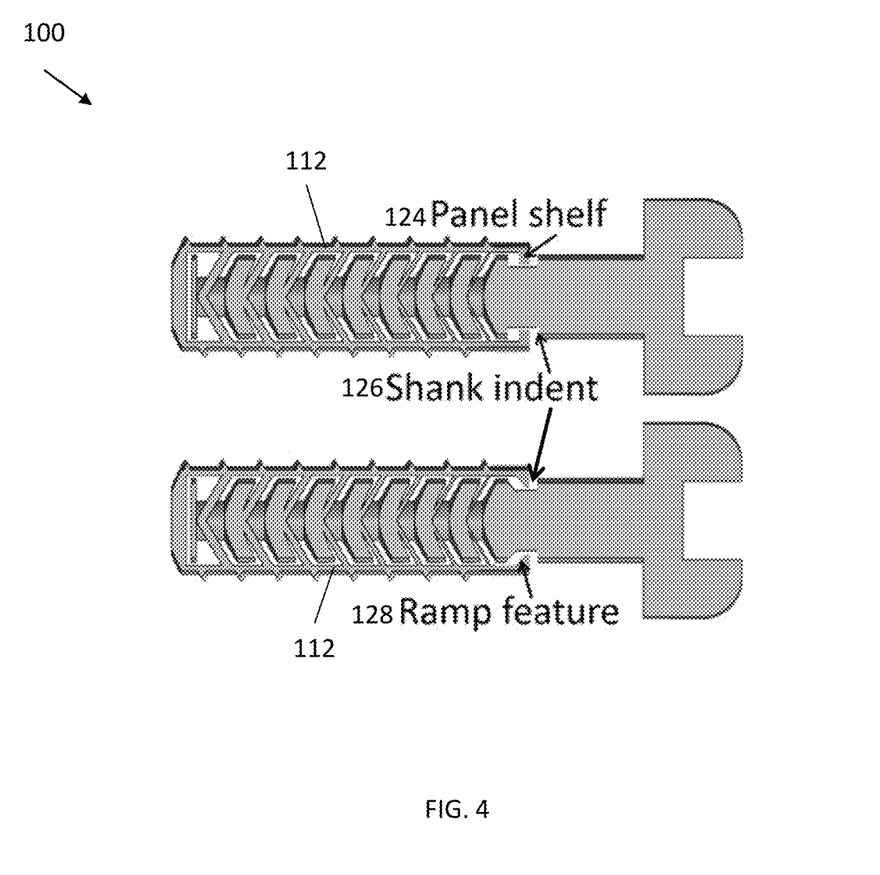
FIG. 4 depicts cross-sectional side views of an exemplary screw with stop features.

Referring now to FIG. 4, screw 100 can include additional structural features that enhance its pullout strength. For example, shank 110 can have a shank indent 126 near the proximal end of threaded panel 112, wherein shank indent 126 is a ring-shaped channel encircling shank 110 having a proximal and a distal wall (FIG. 4, top). The proximal end of threaded panel 112 can have a panel shelf 124 that extends inwards into shank indent 126. When screw 100 is under load and threaded panel 112 is tensioned in a distal direction, the distal wall of shank indent 126 acts as an additional hard stop that panel shelf 124 is blocked by under high load conditions. In another example, the distal wall of shank indent 126 is angled towards the distal end of screw 100 and panel shelf 124 presents an angled surface facing the distal wall of shank indent 126 that is substantially parallel to the distal wall of shank indent 126 (FIG. 4, bottom). When screw 100 is under load and threaded panel 112 is tensioned in a distal direction, the angled distal wall of shank indent 126 pushes panel shelf 124 and threaded panel 112 further outwards under high load conditions to increase anchoring strength.

In some embodiments, screw 100 is suitable for use in medical applications. For example, screw 100 can be used as a pedicle screw or other screw to fasten a medical implant onto a bone. Screw 100 is more compliant than other all-solid screw designs and can be tuned to match the stiffness of a bone to which it is attached. The auxetic behavior of screw 100 also cyclically loads surrounding bone in addition to applying an ever-present anchoring pressure on bone. This loading induces natural bone growth onto the screws exposed surface and will thus accelerate osteointegration. The spaces and crevices in screw 100 can enhance osteointegration through infiltration of osteoblasts or loading with a bone cement or bone graft material.

Figure 5:
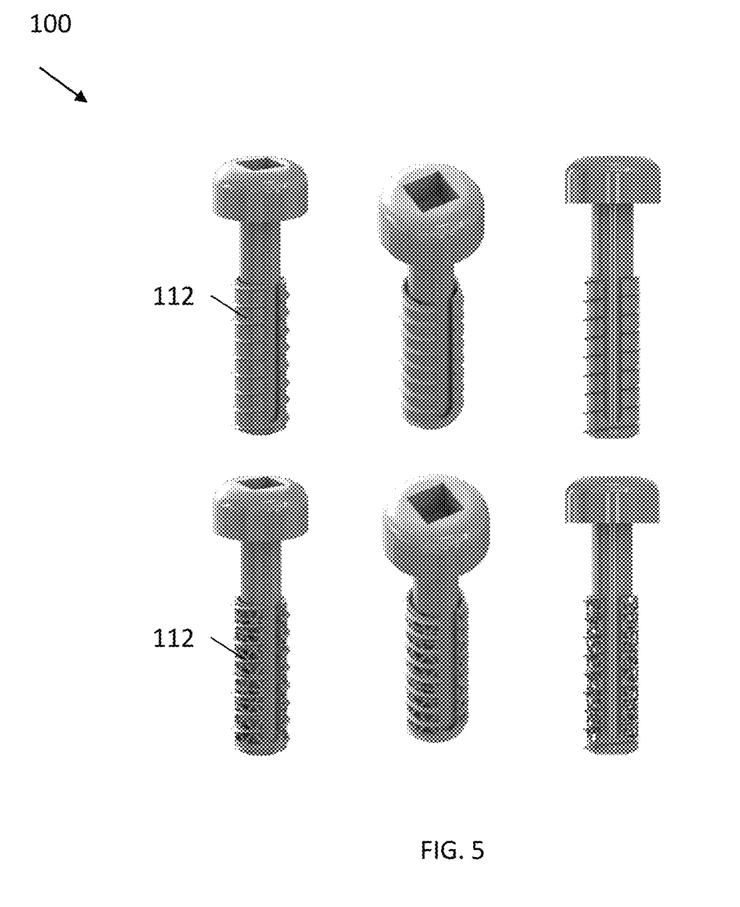
FIG. 5 depicts perspective and side views of exemplary screws.

Referring now to FIG. 5 (bottom), screw 100 can further include one or more textured or perforated surfaces to increase surface area to volume ratio for attachment. Textured surfaces can improve the frictional fit between screw 100 and a substrate hole. Perforated surfaces can also be saturated with glue, resin, or other setting material to enhance the securement of screw 100 in a substrate hole. While threaded panel 112 is depicted in FIG. 5 with triangular perforations or cutouts, it should be appreciated that the perforations or cutouts can have any desired shape or higher ordered pattern, such as an octet truss lattice. The smaller and more numerous the architected features, the more surface area there will be to enhance osteointegration.

The screws of the present invention can be made from any suitable material, including but not limited to metals, polymers, and ceramics. The screws can be fabricated using 3D printing or other additive manufacturing techniques commonly used in the art. In some embodiments, exterior features such as geometry of head 106, screw drive 108, and threading and spacing of threaded panel 112 can be milled or ground after the additive manufacturing process.

High precision additive manufacturing can enable perforated or cutout surfaces to comprise beams and lattices on the order of tens of nanometers or less in thickness and width, strengthening screw 100 and making it more resilient and impervious to fatigue and other failures. The strength-to-weight ratio of head 106 and shank 110 can also be optimized to use mass as efficiently as possible.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compliant self-anchoring screw with auxetic properties comprising:
    a proximal screw head;
    a screw shank extending distally from the screw head;
    a plurality of blade flexures extending from the screw shank in a proximal direction at an angle relative to a longitudinal axis of the screw shank the plurality of blade flexures being linearly aligned to form at least two rows of blade flexures along the screw shank;
    a panel attached to each row of blade flexures; and
    a screw thread positioned on an exterior surface of each panel, the screw thread being continuous across all panels;
    wherein the screw comprises a resting state and a loaded state, wherein the screw shank has a proximal diameter and a distal diameter, the distal diameter defining a central shaft, and wherein the screw shank further comprises one or more rings extending from the central shaft, each ring being positioned immediately distal to a blade flexure.

2. The screw of claim 1, wherein the plurality of blade flexures extend from the central shaft beyond the proximal diameter of the screw shank.

3. The screw of claim 1, wherein the proximal diameter is greater than, equal to, or less than the distal diameter.

4. The screw of claim 1, wherein each blade flexure has a cross-sectional shape that is rectangular or trapezoidal.

5. The screw of claim 1, wherein each blade flexure has a profile that is rectangular or trapezoidal.

6. The screw of claim 1, wherein the plurality of blade flexures comprises varied thicknesses, such that each row of blade flexures is ordered with a thickest thickness at a distal end and a thinnest thickness at a proximal end.

7. The screw of claim 1, wherein a first ring of the one or more rings is positioned at a distal end of the central shaft and a second ring of the one or more rings is positioned at a midpoint of a length of the central shaft.

8. The screw of claim 1, wherein the screw thread is longer at a proximal end and gradually decreases toward a distal end.

9. The screw of claim 1, wherein each panel is positioned equidistantly around the screw shank.

10. The screw of claim 1, wherein the loaded state of the screw tensions each panel in a distal direction relative to the screw head and the screw shank, such that each blade flexure bends outwardly and expands each panel outwards, away from the screw shank.

11. The screw of claim 1, wherein all panels are connected to each other at a distal end to form a distal tip.

12. The screw of claim 11, wherein the distal tip is selected from the group consisting of: a flat end, a slight taper, a pointed tip, a self-tapping tip, and a self-drilling tip.

13. The screw of claim 11, wherein the resting state of the screw maintains a gap between the distal tip and a distal end of the screw shank.

14. A compliant, self-anchoring screw with auxetic properties comprising:
    a proximal screw head;
    a screw shank extending distally from the screw head;
    a plurality of blade flexures extending from the screw shank in a proximal direction at an angle relative to a longitudinal axis of the screw shank the plurality of blade flexures being linearly aligned to form at least two row of blade flexures along the screw shank;
    a panel attached to each row of blade flexures; and
    a screw thread positioned on an exterior surface of each panel, the screw thread being continuous across all panels;
    wherein the screw comprises a resting state and a loaded state, and
    wherein the screw shank comprises an indent encircling the screw shank, the indent forming a distal wall, and wherein each panel comprises a panel shelf that extends into the indent, such that the distal wall blocks the panel shelf when each panel is overtensioned in a distal direction.

15. The screw of claim 14, wherein the distal wall is angled in a distal direction, and wherein the panel shelf of each panel has an angled surface facing the distal wall, such that the distal wall pushes the panel shelf outwards, away from the screw shank, when each panel is overtensioned in a distal direction.

16. A compliant, self-anchoring screw with auxetic properties comprising:
    a proximal screw head;
    a screw shank extending distally from the screw head;
    a plurality of blade flexures extending from the screw shank in a proximal direction at an angle relative to a longitudinal axis of the screw shank the plurality of blade flexures being linearly aligned to form at least two row of blade flexures along the screw shank;
    a panel attached to each row of blade flexures; and
    a screw thread positioned on an exterior surface of each panel the screw thread being continuous across all panels;
    wherein the screw comprises a resting state and a loaded state wherein all panels are connected to each other at a distal end to form a distal tip, and
    wherein the resting state of the screw positions the distal tip flush against a distal end of the screw shank.

17. A compliant, self-anchoring screw with auxetic properties comprising:
    a proximal screw head;
    a screw shank extending distally from the screw head;
    a plurality of blade flexures extending from the screw shank in a proximal direction at an angle relative to a longitudinal axis of the screw shank the plurality of blade flexures being linearly aligned to form at least two row of blade flexures along the screw shank;
    a panel attached to each row of blade flexures; and
    a screw thread positioned on an exterior surface of each panel the screw thread being continuous across all panels;
    wherein the screw comprises a resting state and a loaded state, and
    wherein the loaded state of the screw compresses each panel in a proximal direction relative to the screw head and the screw shank, such that each blade flexure bends inwards and compacts each panel inwards towards the screw shank.

18. A compliant, self-anchoring screw with auxetic properties comprising:
- a proximal screw head;
- a screw shank extending distally from the screw head;
- a plurality of blade flexures extending from the screw shank in a proximal direction at an angle relative to a longitudinal axis of the screw shank the plurality of blade flexures being linearly aligned to form at least two row of blade flexures along the screw shank;
- a panel attached to each row of blade flexures; and
- a screw thread positioned on an exterior surface of each panel the screw thread being continuous across all panels;
- wherein the screw comprises a resting state and a loaded state, and
- wherein the screw shaft, each of the panels, and combinations thereof comprise a textured or perforated surface that increases its surface area to volume ratio.

\* \* \* \* \*